United States Patent [19]

DeMarinis et al.

[11] 4,341,786

[45] Jul. 27, 1982

[54] PHARMACEUTICAL COMPOSITIONS AND METHOD OF PRODUCING CENTRAL ALPHA$_1$ AGONIST ACTIVITY UTILIZING OCTAHYDROBENZO[f]QUINOLINE COMPOUNDS

[75] Inventors: Robert M. DeMarinis, Ardmore; Dinubhai H. Shah, Norristown, both of Pa.

[73] Assignee: SmithKline Corporation, Philadelphia, Pa.

[21] Appl. No.: 239,778

[22] Filed: Mar. 2, 1981

[51] Int. Cl.$^3$ .................... A61K 31/47; C07D 221/10
[52] U.S. Cl. .................................. 424/258; 546/101
[58] Field of Search .......................... 424/258; 546/101

[56] References Cited

FOREIGN PATENT DOCUMENTS 47-34706  9/1972  Japan ................................. 546/101
47-41899 10/1972  Japan ................................. 546/101

OTHER PUBLICATIONS

Cannon, et al., J. Med. Chem., vol. 23, No. 1, pp. 1-5, (01/80).
Chemical Abstracts, vol. 92, 51846n (1980).
Rigid Congeners of Dopamine Based on Octahydrobenzo[f]Quinoline: Peripheral and Central Effects, Joseph G. Cannon, et al., Journal of Medicinal Chemistry, vol. 22, No. 4: 341-347, (1979).

*Primary Examiner*—Donald G. Daus
*Assistant Examiner*—Diana G. Rivers
*Attorney, Agent, or Firm*—Joseph A. Marlino; Richard D. Foggio; Alan D. Lourie

[57] ABSTRACT

Octahydrobenzo[f]quinoline compounds having 7- and 10-substituents are centrally acting alpha$_1$ agonists.

9 Claims, No Drawings

PHARMACEUTICAL COMPOSITIONS AND METHOD OF PRODUCING CENTRAL ALPHA$_1$ AGONIST ACTIVITY UTILIZING OCTAHYDROBENZO[f]QUINOLINE COMPOUNDS

This invention relates to new octahydrobenzo-[f]-quinoline compounds having 7- and 10- substituents. These compounds have pharmacological activity, in particular they are alpha$_1$ agonists.

The catecholamine theory of depression is that the depression is caused by lack of norepinephrine in the synaptic cleft of central noradrenergic nerve endings resulting in inadequate activation of the postsynaptic alpha$_1$ receptor.

The compounds of this invention are capable of producing direct stimulation of central postjunctional alpha$_1$ receptors by mimicking the action of norepinephrine and restoring the normal postsynaptic activity. They are therefore direct acting alpha$_1$ agonists which are associated with antidepressant activity.

The compounds of this invention, and which are the active ingredients of the pharmaceutical compositions and methods of this invention, are represented by the following formula:

Formula 1

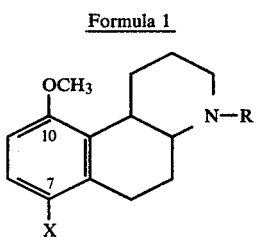

in which:

R is hydrogen or lower alkyl having one to three carbon atoms;

X is methoxy, methylthio or ethylthio; and pharmaceutically acceptable, acid addition salts thereof.

The compounds of this invention are prepared by the following procedure:

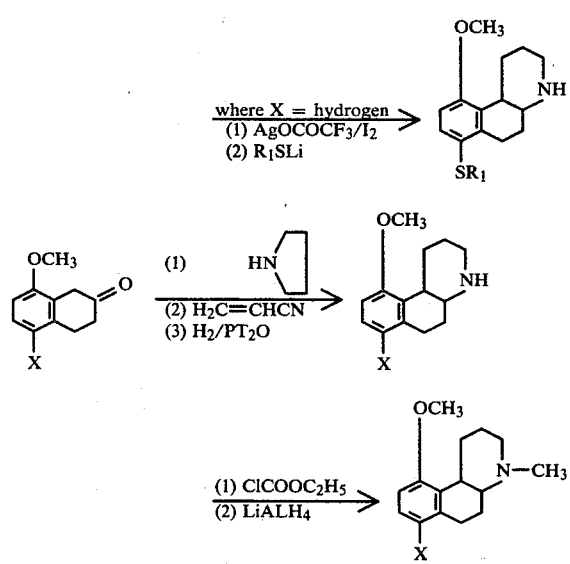

X = hydrogen or methoxy
R$_1$ = methyl or ethyl

According to the above procedure, 5,8-substituted-2-tetralone is converted to the corresponding octahydrobenzo[f]quinoline by forming the enamine, cyanoalkylating, and reductively cyclizing the resulting ketone. Electrophilic substitution at the 7-position of the 10-methoxy octahydrobenzo[f]quinoline is then carried out to yield the substituents as disclosed above. For example, when the alkylthio substituent is desired, the octahydrobenzo[f]quinoline is treated with silver trifluoromethyl acetate and iodine. The iodine is displaced in a further reaction with a lithium alkyl mercaptide. The 4-(N-methyl) derivative is obtained by the reaction of the corresponding N-unsubstituted-7,10-substituted octahydrobenzo[f]quinoline with ethyl chloroformate followed by reduction with lithium aluminum hydride.

The compounds of this invention may exist as cis and trans isomers and it is the intent of this invention to include all possible isomers and mixtures thereof. The isomers can be separated by chromatography of the corresponding N-benzyl amines and subsequent removal of the benzyl group, advantageously by hydrogenolysis over Pd/c.

Pharmaceutically acceptable acid addition salts of the compounds of Formula 1 are formed with organic and inorganic acids by methods known to the art. The base is treated with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

The basic activity of the compounds of this invention is demonstrated in vitro by determining the selective postjunctional alpha$_1$ adrenergic agonist activity using the isolated rabbit ear artery. The assay procedure is described by Steinsland et al. J. Pharm. Exp. Ther. 184:346–356, 1973. Briefly, this test comprises sacrificing a white rabbit and removing the central ear artery. The artery is cannulated at both ends and placed in a perfusion chamber. The artery is simultaneously perfused intraluminally and superfused extraluminally with Krebs solution. The compound to be tested can be administered by means of either the intraluminal or extraluminal flow. The sympathetic nerve is excited at four minute intervals by field stimulation. The selective alpha$_1$ agonist activity is measured as the ability to increase perfusion pressure (mm Hg.) without inhibiting response to sympathetic nerve stimulation.

A quantitation of postjunctional alpha$_1$ agonist activity (EC$_{50}$) is determined for compounds showing activity in the above test. This is accomplished by employing an isolated segment of rabbit ear artery. The segment is mounted in a chamber superfused with oxygenated Krebs solution. The segment is suspended between two tungsten wires, one attached to the chamber, the other to a force-displacement transducer so that smooth muscle tension can be measured directly. Before administration of the test drug, norepinephrine is administered in increasing concentration ($10^{-8}$M to $3\times10^{-6}$M) to determine maximum response of the artery. The dose required to produce 50% of the maximum response is the $EC_{50}$.

The $EC_{50}$ of a preferred compound of this invention, 7,10-dimethoxy-1,2,3,4,4a,5,6,10-b-octahydrobenzo[f]quinoline hydrochloride is $1.9\times10^{-7}$M.

Octahydrobenzo[f]quinoline compounds having 7,8-dimethoxy substituents are generally known in the art. These compounds are disclosed in J. Med. Chem. 22(4):341–347, 1979 as dopaminergic agents which induce emesis.

The pharmaceutical compositions of this invention having $alpha_1$ agonist activity comprise a pharmaceutical carrier and, as the active ingredient, an octahydrobenzo[f]quinoline compound of Formula 1. The active ingredient will be present in the compositions of this invention in an effective amount to produce $alpha_1$ agonist activity.

Preferably, the compositions of this invention contain the active ingredient of Formula 1 in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of producing $alpha_1$ agonist activity according to this invention comprises administering to an animal in an amount sufficient to produce $alpha_1$ agonist activity an octahydrobenzo[f]quinoline compound of Formula 1.

Preferably, the compounds of Formula 1 are administered in conventional dosage unit forms prepared by combining an appropriate dose of the compound with standard pharmaceutical carriers.

Preferably, the active ingredient of Formula 1 will be administered in a daily dosage regimen of from about 100 mg. to about 2000 mg., most preferably from about 200 mg. to about 1000 mg. Advantageously, equal doses will be administered preferably two to three times per day. When the administration is carried out as described above, $alpha_1$ agonist activity is produced.

The route of administration of the pharmaceutical compositions of this invention and in accordance with the methods of this invention is internal, either parenteral or preferably oral, in an amount to produce the desired biological activity.

The following examples are not limiting but are illustrative of this invention.

EXAMPLE 1

A mixture of 0.8 g. (3.9 mmol) of 5,8-dimethoxy-2-tetralone and 0.4 g. (5.8 mmol) of pyrrolidine in 50 ml. of toluene was refluxed with a trace of p-toluene sulfonic acid for 3 hours. The solvent was removed to leave 0.8 g. of enamine. A mixture of 0.5 g. (1.9 mmol) of the enamine, 1 ml. of acrylonitrile and 6 ml. of dioxane was refluxed for 20 hours. It was treated with 15 ml. of water and 5 ml. of acetic acid and refluxed for 2 hours. The mixture was extracted with ether and the extracts washed with 3 N hydrochloric acid, 10% sodium hydroxide and water, dried over magnesium sulfate and evaporated to give 0.3 g. of a solid. This was dissolved in 25 ml. of ethanol and 5 ml. of acetic acid and hydrogenated at 54 psi for 4 hours over 50 mg. of platinum oxide. The catalyst was removed by filtration and the filtrate diluted with 1 N hydrochloric acid. It was extracted with ether, made basic with 10% sodium hydroxide solution and extracted again with ether. The basic ethereal extract was dried over magnesium sulfate, filtered and the free base product was treated with excess ethereal hydrogen chloride. The resulting precipitate was removed by filtration and triturated with acetone to give a mixture of the cis-trans isomers of 7,10-dimethoxy-1,2,3,4,4a,5,6,10-b-octahydro-benzo[f]quinoline hydrochloride as a slightly pink solid.

To 0.45 g. of the above mixture in 10 ml. of methylene chloride and 0.32 g. of sodium hydroxide in 10 ml. of water was added 0.332 g. (0.00237 m.) of benzoyl chloride and the mixture was stirred for 90 minutes. The organic layer was separated and washed with 10% sodium hydroxide, 3 N hydrochloric acid and water, dried over magnesium sulfate and evaporated to give the corresponding cis-trans benzamides. The benzamides were refluxed for five hours in ether with 0.518 g. (0.00136 m.) of lithium aluminum hydride to give the corresponding cis-trans N-benzylamines. The mixture of N-benzylamines was separated on a silica gel column packed in 7:3 cyclohexane:ether containing one percent of triethylamine and eluting with 7:3 cyclohexane ether. The faster moving spot was separated to yield cis-N-benzylamine. Removal of the slower moving spot yielded the trans-N-benzylamine. These pure isomers were then debenzylated by hydrogenation in methanol/hydrochloric acid and Pd/c catalyst to give the pure cis-7,10-dimethoxy-1,2,3,4,4a,5-6,10-b-octahydrobenzo[f]quinoline hydrochloride, m.p. 305° C. and the corresponding trans-isomer, m.p. 256° C.

EXAMPLE 2

When 8-methoxy 2-tetralone is substituted for the 5,8-dimethoxy tetralone of Example 1, the corresponding 10-methoxy-1,2,3,4,4a,5,6,10-b-octahydrobenzo[f]quinoline hydrochloride is obtained. A suspension of 284 mg. (1 mmol) of the hydrochloride and 844 mg. (4 mmol) of silver trifluoroacetate in 25 ml. of methylene chloride is stirred at room temperature while 508 mg. (2 mmol) of iodine in 25 ml. of methylene chloride is added dropwise over 10 minutes. The mixture is stirred for 30 minutes, filtered through celite and the filtrate washed with water, dried and evaporated to give a solid. A mixture of 343 mg. (1 mmol) of the iodide, 270 mg. (5 mmol) of lithium methylmercaptide and 214 mg. (1.5 mmol) of cuprous oxide was heated in 10 ml. of dimethylformamide to 80° C. for 3 hours. It is cooled, diluted with 50 ml. of water and extracted with methylene chloride. The organic layer is dried and evaporated to leave an oil (the free base product) which is taken up in ether and treated with excess hydrogen chloride in ether. The resulting precipitate is collected and dried to yield 7-methylthio-10-methyoxy-1,2,3,4,4a,5,6,10-b-octahydrobenzo[f]quinoline hydrochloride.

EXAMPLE 3

When lithium ethylmercaptide is substituted for lithium methylmercaptide in the procedure of Example 2, 7-ethylthio-10-methoxy-1,2,3,4,4a,5,6,10-b-octahydrobenzo[f]-quinoline hydrochloride is formed.

EXAMPLE 4

To a solution of 0.50 g. (2 mmol) of cis-7,10-dimethoxy, 1,2,3,4,4a,5,6,10-b-octahydrobenzo[f]quinoline in 1 ml. of pyridine was added 2.2 g. (20 mmol) of ethylchloroacetate. After 1 hour 25 ml. of dilute hydrochloric acid was added and the solution extracted with methylene chloride. The organic extracts were washed with water, dried and evaporated to give an oil. This was dissolved in 30 ml. of dry ether and treated with 893 mg. (23 mmol) of lithium aluminum hydride. It was refluxed for 3 hours, cooled and hydrolyzed by the careful addition of 1:2:4 water, 10% sodium hydroxide and water. The mixture was filtered and the filtrate dried, and treated with excess ethereal hydrogen chloride. The resulting precipitate was removed by filtration to give a white solid, 4-methyl-7,10-dimethoxy-1,2,3,4,4a,5,6,10-b-octahydrobenzo[f]quinoline hydrochloride as the cis-isomer, 131°–135° C.

EXAMPLE 5

| Ingredients | Mg./Capsule |
|---|---|
| Cis-7,10-dimethoxy 1,2,3,4,4a,5,6,-10-b-octahydrobenzo-[f]quinoline (as the hydrochloride salt) | 150 |
| Lactose | 150 |

The above ingredients are mixed and filled into a hard gelatin capsule.

One capsule is given three times a day.

EXAMPLE 6

| Ingredients | Mg./Tablet |
|---|---|
| Trans-7,10-dimethoxy 1,2,3,4,4a-5-6-10-b-octahydrobenzo-[f]quinoline (as the hydrochloride salt) | 50 |
| Calcium Sulfate Dihydrate | 150 |
| Sucrose | 25 |
| Starch | 15 |
| Talc | 5 |
| Stearic Acid | 3 |

The sucrose, calcium sulfate and octahydrobenzoquinoline are thoroughly mixed and granulated with hot 10% gelatin solution. The wetted mass is passed through a No. 6 mesh screen directly onto drying trays.

The granules are dried at 120° C. and passed through a No. 20 mesh screen, mixed with starch, talc and stearic acid and compressed into tablets.

Two tablets are administered three times a day.

What is claimed is:

1. A pharmaceutical composition in dosage unit form having alpha$_1$ agonist activity comprising a pharmaceutical carrier and an effective amount of a compound of the formula:

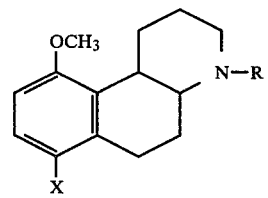

in which:

R is hydrogen or lower alkyl having 1 to 3 carbon atoms;

X is methoxy, methylthio or ethylthio; or a pharmaceutically acceptable acid addition salt thereof.

2. The pharmaceutical composition of claim 1 in which X is methoxy.

3. The pharmaceutical composition of claim 2 in which R is hydrogen, being the compound 7,10-dimethoxy-1,2,3,4,4a,5,6,10-b-octahydro[f]quinoline or a pharmaceutically acceptable acid addition salt thereof.

4. The pharmaceutical composition of claim 3 in which the cis isomer of the compound is present.

5. The pharmaceutical composition of claim 3 in which the trans isomer of the compound is present.

6. A method of producing alpha$_1$ agonist activity which comprises administering to an animal requiring said treatment an amount sufficient to produce said activity of a chemical compound of the formula:

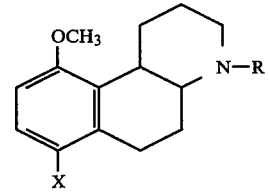

in which:

R is hydrogen or lower alkyl having 1 to 3 carbon atoms;

X is methoxy, methylthio or ethylthio; or a pharmaceutically acceptable acid addition salt thereof.

7. The method of claim 6 in which X is methoxy.

8. The method of claim 7 in which R is hydrogen, being the compound 7,10-dimethoxy-1,2,3,4,4a,5,6,10-b-octahydro[f]quinoline or a pharmaceutically acceptable acid addition salt thereof.

9. The method of claim 6 which comprises administering a dosage unit containing from about 50 mg. to about 1000 mg.

* * * * *